Figure 1:
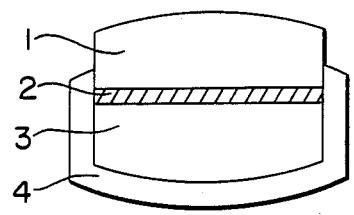

United States Patent [19]

Conte et al.

[11] Patent Number: 4,865,849

[45] Date of Patent: Sep. 12, 1989

[54] TABLET FOR PHARMACEUTICAL USE ABLE TO RELEASE ACTIVE SUBSTANCES AT SUCCESSIVE TIMES

[75] Inventors: Ubaldo Conte, Busto Arsizio; Aldo La Manna; Paolo Colombo, both of Pavia, all of Italy

[73] Assignee: Pharmidea, Milan, Italy

[21] Appl. No.: 139,635

[22] Filed: Dec. 30, 1987

[30] Foreign Application Priority Data

Jan. 13, 1987 [IT] Italy .................. 19064 A/87

[51] Int. Cl.$^4$ ............................................. A61K 9/46
[52] U.S. Cl. ..................... 424/466; 424/470; 424/471; 424/472; 424/480; 424/482; 427/3
[58] Field of Search ............... 424/472, 471, 470, 480, 424/482, 466; 427/3

[56] References Cited

U.S. PATENT DOCUMENTS

| | | | |
|---|---|---|---|
| 3,317,394 | 5/1967 | Fryklof et al. | 424/472 |
| 4,139,589 | 2/1979 | Beringer et al. | 424/440 X |
| 4,267,138 | 5/1981 | Dobo et al. | 424/482 X |
| 4,753,790 | 6/1988 | Silva et al. | 424/482 X |
| 4,756,911 | 7/1988 | Drost et al. | 424/472 X |

FOREIGN PATENT DOCUMENTS 2123289 2/1984 United Kingdom ............... 424/472

*Primary Examiner*—Thurman K. Page
*Attorney, Agent, or Firm*—Arnold, White & Durkee

[57] ABSTRACT

A tablet for pharmaceutical use able to release active substances at successive times, comprising at least; a first layer containing a portion of the active substance with suitable excipients, a barrier layer of polymer material gellable and/or soluble in water and/or aqueous liquids, which is interposed between said first layer and a third layer containing the remaining portion of active substance with suitable excipients, said barrier layer and said third layer being housed in a casing consisting of polymer material impermeable and insoluble in water or soluble in an alkaline environment.

That part of the active substance not inserted in the casing is immediately available for dissolving, whereas the part inserted in the casing is available only after dissolution or rupture of the barrier layer and/or after solubilization of the casing.

11 Claims, 1 Drawing Sheet

TABLET FOR PHARMACEUTICAL USE ABLE TO RELEASE ACTIVE SUBSTANCES AT SUCCESSIVE TIMES

This invention relates to a tablet for a pharmaceutical use able to release active substances at successive times.

More specifically, the invention relates to a multi-layer tablet able to release different portions of the same or of different substances at successive times into the aqueous fluid with which it comes into contact.

The invention is particularly suitable for use in the medicinal field but can be generally used in all sectors in which active substances have to be released at different times spaced apart by a predetermined time interval, such as in the fertilizer, herbicide and other sectors.

It is well known that the success of a therapy depends not only on the correct choice of medicament but also on whether its formulation is optimum from the technical and biopharmaceutical viewpoint.

In some cases the active substance must be released from the pharmaceutical form at constant rate to enable a constant hematic concentration within a therapeutically effective range to be maintained for the entire duration of treatment. This result can be obtained by using pharmaceutical forms of controlled release type from which the active principle is released at a constant rate for the time necessary to obtain the desired effect.

In other cases a constant hematic concentration of the medicament is not suitable; in this respect, certain morbid symptoms such as rheumatic and cardiac illnesses require high hematic concentrations to be reached for a limited time period.

This result can be easily obtained by frequently administering pharmaceutical forms which give instant release of the active substances, to thus define a complex posology scheme which is however not easily implemented by the patient.

With the present invention we have conceived a new pharmaceutical form which enables the active substances contained in it to be released in successive spaced-apart stages, to therefore obtain high hematic medicament levels at successive time intervals.

In this manner the posology scheme is simplified and the acute pain symptomatology manifested in these illnesses at determined intervals (such as morning pain in rheumatic illnesses) can be more appropriately resolved.

Basically, the tablet of the present invention enables the number of administrations of active substance to be reduced, with undoubted practical advantages.

The tablet for releasing active substances at successive times according to the invention is characterised by comprising at least: a first layer containing a portion of the active substance and suitable excipients, a barrier layer of polymer material gellable and/or soluble on contact with water and/or aqueous liquids, which is interposed between said first layer and a third layer containing the remaining portion of active substance with suitable excipients, said barrier layer and said third layer being housed in a casing consisting of polymer material impermeable to and insoluble in water or soluble in an alkaline environment.

These and other characteristics and advantages of the tablet according to the invention will be more apparent from the detailed description of preferred embodiments given hereinafter by way of non-limiting example.

A schematic representation of one embodiment of the tablet according to the present invention is shown in FIG. 1 in which the reference numerals 1, 2, and 3 indicate the first, second and third tablet layer respectively, and 4 indicates the casing, the second layer being obviously the barrier layer.

In said embodiment, the tablet of the present invention therefore consists of two separate deposits of active substance 1 and 3, separated from each other by a layer 2 of gellable and/or soluble polymer material.

The tablet can also consist of more than two of said deposits of active substance separated from each other by layers of said polymer material, and in addition the active substance can be of the same or different type in the various deposits or more simply can be in the form of a single layer of active substance enclosed in the casing and separated from the external environment by a layer of said gellable and/or soluble polymer material.

Moreover, the barrier layer can contain an active substance the same as or different from that contained in the other layers.

The active substance release mechanism is the following: on contact with water or aqueous liquid, the uncovered part 1 of the tablet rapidly disintegrates; this therefore results in release of the first medicament portion, leaving as residue the casing 4 closed by the barrier layer 2 and containing the second medicament portion in 3.

At this point the barrier layer comes into contact with the water and interacts with it; this interaction is gradual, in the sense that the water penetrates at a rate controlled by the components of the barrier layer itself.

The time required for the barrier layer to be traversed by the water is controlled not only by the composition but also by the thickness of the barrier. The result of this contact between the water and barrier is that the barrier is converted from a solid into a viscous gel with consequent weakening of its rupture resistance properties. When a sufficient quantity of water has passed through the barrier and made contact with the layer 3, the materials contained in this layer swell, so destroying the barrier layer 2 and allowing the contents to escape.

The medicament release mechanism is therefore based in practice on successive interaction of the various material layers with water in the following sequence:

rapid interaction of the unprotected part 1 with release of the first medicament portion, slow interaction of the barrier layer 2 and its gelling, rapid interaction of the remainder 3 with development of a force able to demolish the gelled barrier and release the second medicament portion.

The described mechanism also applies to the other layers of a tablet having a larger number of layers.

The rate of gelling and/or of solubilization of the barrier layer and/or of the casing is the factor which controls the release of the second portion of active substance.

The rate of release of the active substance from the layers containing it can be varied according to therapeutic needs, and this can be done by varying the composition of the layer concerned.

Each layer of active substance contains, in mixture with the active substance, materials which on contact with water and/or aqueous liquids are able to develop a disintegration force by swelling or by gas formation.

This disintegration force constitutes the source of energy able to determine the release of the active substance from the deposit containing it.

Materials able to supply this disintegration force are those of the so-called "superdisintegrator" class and are usually polymers of natural or synthetic origin for human and veterinary pharmaceutical use.

These materials comprise for example: carboxymethylamide, cross-linked sodiumcarboxymethylcellulose, cross-linked polyvinylpyrrolidone, and cross-linked hydroxypropylemthylcellulose.

Depending on the characteristics of the active substance, inorganic substances can also be used as disintegrators, such as bases and/or acids which when in contact with water are able to react chemically with the active substance or with other excipients of the formulation to give rise to gaseous substances which lead to the rapid disintegration of the layer and thus to the release of the active principle.

Sodium bicarbonate, sodium carbonate, magnesium peroxide etc. are the preferred acids and bases.

In addition to the active substance and disintegration substances, other materials can be used in the formulation which are able to give the mixture the characteristics necessary for its transformation into its finished form.

A basic characteristic of the constituent mixtures of the individual layers is that they are able to be easily compressed or compacted in accordance with the known art.

In each layer containing the active substance, the quantity of swellable material and/or material able to cause disintegration of the layer when it comes into contact with water is between 1% and 95% of the total weight of the layer. The layer composition can also comprise other so-called excipients such as diluents, lubricants, dyes etc., such as magnesium stearate, talc, colouring and the like in a quantity variable from 0.5% to 90%. The active substance present in an individual layer is between 0.1 and 95% of the weight of the layer.

The active substance itself can be prepared in microencapsulated form, i.e. in solid particles covered with polymer material able to transfer the active substance gradually and/or in accordance with the pH variations of the gastro-intestinal tract.

For the barrier layer, polymers are used chosen from cellulose derivatives such as hydroxypropylmethylcellulose, methylcellulose or polyvinylalcohols of various molecular weights, and other excipients can be added such as mannitol, talc, polyvinylpyrrolidone and magnesium stearate.

The casing generally consists of filmogen polymer substances insoluble in and impermeable to water, and can be natural, synthetic or semisynthetic substances such as ethylcellulose, cellulose-acetate-propionate, methacrylic polymers, acrylic and methacrylic copolymers and polyalcohols. Water-insoluble polymers are preferably used, but in certain embodiments polymers soluble in an alkaline environment can be used to facilitate destruction of the casing when in the enteric tract. Biodegradable polymers can also be used.

The tablets are formed by a multilayer tablet press able to exert in the final compression stage a pressure of about 3000 kg/cm$^2$.

The mixture for forming the casing can be applied by various methods such as spraying, compression or immersion, or the tablet parts can be inserted into a preformed casing.

EXAMPLE 1

Preparation of tablets containing ibuprofen as active substance.

(a) Preparation of ibuprofen granulate.

To prepare 1000 tablets the following materials were used in the quantities stated:

| | |
|---|---|
| Ibuprofen | 600 g |
| Corn starch | 120 g |
| Methylcellulose | 4.5 g |

The ibuprofen and corn starch were poured into a powder mixer and the mixture wetted with a 2.5% solution of methycellulose in 1:1 ethanol:water using about 180 ml of solution. The mixture when wetted homogeneously was forced through an 800 μm screen to obtain a granulate which after partial drying was passed through a 420 μm screen in accordance with the known art. The granulate was further dried in a tray drier until of constant weight, after which the following were added:

| | |
|---|---|
| sodium bicarbonate | 15 g |
| sodium carboxymethylamide (Primojel) | 15 g |
| cross-linked polyvinylpyrrolidone (Polyplasdone) | 15 g |
| magnesium stearate | 4 g |

The component mixture was mixed until a homogeneous product was obtained.

(b) Preparation of barrier layer material.

The following were used to prepare 1000 barrier layers for tablet preparation:

| | |
|---|---|
| Hydroxypropylmethylcellulose (low molecular weight-Methocel) | 7.5 g |
| Hydroxypropylmethylcellulose (medium molecular weight-Methocel) | 2.5 g |
| Mannitol | 20 g |
| Talc | 14 g |
| Polyvinylpyrrolidone | 6 g |
| Yellow colouring | 1 g |
| Mg stearate | 0.5 g |

The hydroxypropylmethylcellulose, mannitol, talc and yellow colouring were mixed in a powder mixer; the mixture was wetted with a solution of polyvinylpyrrolidone in alcohol and the wet mass was forced through a 420 μm screen.

The granulate was dried in an oven and was then mixed with magnesium stearate.

(c) Preparation of tablets.

The tablets were prepared without their casing using a multilayer tablet press with three loading stations; the first and third station were fed with the granulate containing ibuprofen prepared as described under point (a), the second loading station being fed with the polymer granulate prepared for the barrier layer as indicated under point (b).

The machine, fitted with circular dished punches of 13 mm diameter, was adjusted to feed a granulate quantity equivalent to 300 mg of active substance from stations 1 and 3 and granulate quantity of about 100 mg from station 2. The machine pressure was adjusted to allow a pressure of about 3000 kg/cm$^2$ to be exerted in the final compression stage.

Operating as described, at the end of the working cycle convex-based cylindrical tablets were obtained weighing about 900 mg and having two layers of active substance and a regular, homogeneous barrier layer of gellable polymer material, separating the two layers of active substance.

(d) Application of the casing.

The tablets obtained as described were positioned in a suitable container provided with regularly positioned circular cavities able to only partly contain a prepared tablet when positioned horizontally, to leave an exposed portion comprising a layer of active substance and the barrier layer.

Using a suitable spray system, the exposed surface of the tablets was sprayed with a solution consisting of:

| | |
|---|---|
| Ethylcellulose (Ethocel) | 16 g |
| Diethyl phthalate | 4 g |
| Ethanol | 10 g |
| Ethyl acetate | 12 g |
| Toluene | 45 g |
| Butyl acetate | 13 g |

(e) "In vitro" evaluation of tablet characteristics.

(1) disintegration test.

The apparatus of U.S.P. XXI was used to evaluate the tablet disintegration rate.

6 tablets were placed in the baskets and the prescribed procedure was followed using water at 37° C. as the disintegration fluid.

The first tablet layer containing the first medicament portion (300 mg) disintegrated in 5 minutes, after which time the second medicament portion contained in the third layer was completely unaltered, this portion being protected on its top by the gellable polymer barrier and on its sides and bottom by the impermeable and insoluble polymer membrane.

As the disintegration test proceeded a slow hydration of the barrier layer was noted, with an increase in volume of the barrier, gelling and weakening of the layer and slow erosion and/or solubilization.

During this stage the barrier layer became progressively permeable to the disintegration liquid, to enable water, after a time of about 0.5-1 hours, to come into contact with the second layer of the system containing the second portion of active principle.

When the water or aqueous fluid comes into contact with the third layer it swells to destroy the gelled barrier, with emergence of the ibuprofen particles in a time of about 15 minutes.

During the entire disintegration process the insoluble and impermeable polymer coating around the tablet preserves its characteristics and therefore at the end of the disintegration process it remains as a completely empty cylindrical container.

(2) Dissolution tests.

The "in vitro" tests to determine the release of active substance from the tablets were conducted using as the dissolution apparatus the six-position basket scheduled for the U.S.P. XXI disintegration test.

1000 ml of simulated intestinal fluid at pH 7.2 and at a temperature of 37° C. were used as the dissolution fluid.

Using the tablets prepared as in Example 1, the following results were obtained:

| time | % fraction released |
|---|---|
| (minutes) | (of the 1st portion of 300 mg of active substance contained in the 1st layer) |
| 2 | 50% |
| 4 | 75% |
| 6 | 85% |
| 8 | 92% |
| 10 | 100 |
| 35 | Membrane hydration |
| | % fraction released |
| | (of the 2nd portion of 300 mg of active substance contained in the 3rd layer) |
| 40 | 30% |
| 50 | 100% |

(3) "In vivo" evaluation of the tablets

The tablets prepared as in Example 1 were administered to healthy volunteers and gave the following plasmatic levels of active substance:

| time (hours) | plasmatic concentration (mcg/ml) |
|---|---|
| 1 | 25.8 |
| 2 | 22.3 |
| 4 | 14.3 |
| 6 | 5.7 |
| 8 | 8.1 |
| 10 | 9.6 |
| 12 | 10.5 |
| 24 | 4.0 |

EXAMPLE 2

Preparation of tablets containing propanolol HC1 as active substance (a) Preparation of propanolol HCl granulate.

To prepare 10000 tablets the following materials were used in the quantities stated:

| | |
|---|---|
| Propanol HCl | 400 g |
| Corn starch | 1000 g |
| Methylcellulose | 10 g |
| Sodium laurylsulphate | 5 g |

The propanolol HCl and corn starch sieved to 420μ were poured into a powder mixer and the mixture wetted with a 1.3% solution of methylcellulose in water containing the stated quantity of sodium laurylsulphate. The mixture when wetted homogeneously was forced through an 800μ screen to obtain a granulate which after partial drying was passed through a 420μ screen in accordance with the known art. The granulate was further dried in a tray drier until of constant weight, after which the following were added:

| | |
|---|---|
| sodium carboxymethylamide (Primojel) | 110 g |
| corn starch | 260 g |
| cross-linked polyvinylpyrrolidone (Polyplasdone) | 46 g |
| microcrystalline cellulose (Avicel pH 101) | 185 g |
| magnesium stearate | 15 g |

The component mixture was mixed until a homogeneous product was obtained.

(b) Preparation of barrier layer material.

The following were used to prepare 10000 barrier layers for tablet preparation:

| | |
|---|---|
| Hydroxypropylmethylcellulose low molecular weight-Methocel KM4) | 97.5 g |

| | |
|---|---|
| Hydroxypropylmethylcellulose (medium molecular weight-Methocel K15M) | 32.5 g |
| Mannitol | 260.0 g |
| Talc | 182.0 g |
| Polyvinylpyrrolidone | 78.0 g |
| Yellow colouring | 13.0 g |
| Mg stearate | 6.5 g |

The hydroxypropylmethylcellulose, mannitol, talc and yellow colouring were mixed in a powder mixer; the mixture was wetted with a solution of polyvinylpyrrolidone in alcohol and the wet mass was forced through a 420μ screen. The granulate was dried in an oven and was then mixed with magnesium stearate.

(c) Preparation of propanolol HCl tablets.

The tablets were prepared without their casing using a multilayer tablet press with three loading stations; the first and third station were fed with the granulate containing propanolol HCl prepared as described under point (a), the second loading station being fed with the polymer granulate prepared for the barrier layer as indicated under point (b). The machine, fitted with circular flat punches of 10 mm diameter, was adjusted to feed a granulate quantity of 200 mg equivalent to 40 mg of active substance from stations 1 and 3 and a quantity of about 65 mg from station 2.

The machine pressure was adjusted to allow a pressure of about 3000 kg/cm$^2$ to be exerted in the final compression stage. Operating as described, at the end of the working cycle flat-based cylindrical tablets were obtained weighing about 465 mg and having two layers of active substance and a regular, homogeneous barrier layer of gellable polymer material, separating the two layers of active substance.

(d) Application of the casing.

The tablets obtained as described were placed in a suitable container provided with regularly positioned circular cavities able to only partly contain a prepared tablet when positioned horizontally, to leave an exposed portion comprising a layer of active substance and the barrier. Using a suitable spray system, the exposed surface of the tablets was sprayed with a solution consisting of:

| | |
|---|---|
| copolymer of acrylic and methacrylic acids (Eudragit S 100) | 5.0 g |
| castor oil | 0.5 g |
| acetone | 37.8 g |
| isopropanol | 56.7 g |

(e) "In vitro" evaluation of tablet characteristics.

(1) disintegration test.

The apparatus of U.S.P. XXI was used to evaluate the tablet disintegration rate. 6 tablets were placed in the baskets and the prescribed procedure was followed using gastric fluid (pH 1.2) at 37° C. as the disintegration fluid.

The first tablet layer containing the first medicament portion (40 mg) disintegrated in 9 minutes, after which time the second medicament portion contained in the third layer was completely unaltered, this portion being protected on its top by the gellable polymer barrier and on its sides and bottom by the impermeable and insoluble polymer membrane.

As the disintegration test proceeded a slow hydration of the barrier layer was noted, with an increase in volume of the barrier, gelling and weakening of the layer and slow erosion and/or solubilization.

During this stage the barrier layer became progressively permeable to the disintegration liquid, to enable water, after a time of about 0.5–1 hours, to come into contact with the second layer of the system containing the second portion of active principle.

When the water or aqueous fluid comes into contact with the third layer it swells to destroy the gelled barrier, with emergence of the propanolol HCl particles contained in the second layer. During the entire disintegration process the insoluble and impermeable polymer coating around the tablet preserves its characteristics and therefore at the end of the disintegration process it remains a a completely empty cylindrical container.

(2) Dissolution tests.

The "in vitro" test to determine the release of active substance from the tablets were conducted using as the dissolution apparatus the six-position basket prescribed for the U.S.P. XXI disintegration test. 1000 ml of simulated gastric fluid at pH 1.2 and at a temperature of 37° C. were used as the dissolution fluid. Using the tablets prepared as in Example 2, the following results were obtained:

| time (minutes) | % released (*) |
|---|---|
| 2 | 18.4% |
| 4 | 33.5% |
| 6 | 44.0% |
| 8 | 52.5% |
| 10 | 58.8% |
| 15 | 73.0 |
| 20 | 85.0 |
| 35 | Membrane hydration |
| | % released (°) |
| 5 | 4.6% |
| 25 | 10.6% |
| 45 | 18.3% |
| 65 | 63.0% |
| 75 | 74.8 |
| 85 | 81.4% |

(*) Of the first portion of 40 mg of active substance contained in the first layer.
(°) Of the second portion of 40 mg of active substance contained in the third layer.

EXAMPLE 3

Preparation of tablets containing acid indomethacin as active substance (a) Preparation of acid indomethacin granulate.

To prepare 10000 tablets the following materials were used in the quantities stated:

| | |
|---|---|
| Acid indomethacin | 350 g |
| Corn starch | 1000 g |
| Methylcellulose | 10 g |
| Sodium laurylsulphate | 5 g |

The indomethacin and corn starch sieved to 420μ were poured into a powder mixer and the mixture wetted with a 1.3% solution of methylcellulose in water containing the stated quantity of sodium laurylsulphate. The mixture when wetted homogeneously was forced through an 800μ screen to obtain a granulate which after partial drying passed through a 420μ screen in accordance with the known art.

The granulate was further dried in a tray drier until of constant weight, after which the following were added:

| | |
|---|---|
| sodium carboxymethylamide (Primojel) | 110 g |
| corn starch | 260 g |
| cross-linked polyvinylpyrrolidone (Polyplasdone) | 46 g |
| magnesium stearate | 15 g |

The component mixture was mixed until a homogeneous product was obtained.

(b) Preparation of barrier layer material.

The following were used to prepare 10000 barrier layers for tablet preparation:

| | |
|---|---|
| hydroxypropylmethylcellulose (low molecular weight-Methocel KM4) | 97.5 g |
| hydroxypropylmethylcellulose (medium molecular weight-Methocel K15M) | 32.5 g |
| mannitol | 260.0 g |
| talc | 182.0 g |
| polyvinylpyrrolidone | 78.0 g |
| yellow colouring | 13.0 g |
| Mg stearate | 6.5 g |

The hydroxypropylmethylcellulose, mannitol, talc and yellow colouring were mixed in a powder mixer; the mixture was wetted with a solution of polyvinylpyrrolidone in alcohol and the wet mass was forced through a 420μ screen. The granulate was dried in an oven and was then mixed with magnesium stearate.

(c) Preparation of acid indomethacin tablets.

The tablets were prepared without their casing using a multilayer tablet press with three loading stations; the first and third station were fed with the indomethacin granulate prepared as described under point (a), the second loading station being fed with the polymer granulate prepared for the barrier layer as indicated under point (b). The machine, fitted with circular flat punches of 10 mm diameter, was adjusted to feed a granulate quantity of 180 mg equivalent to 35 mg of active substance from stations 1 and 3 and a quantity of about 65 mg from station 2.

The machine pressure was adjusted to allow a pressure of about 3000 kg/cm$^2$ to be exerted in the final compression stage. Operating as described, at the end of the working cycle flat-based cylindrical tablets were obtained weighting about 425 mg and having two layers of active substance and a regular, homogeneous barrier separating the two layers of active substance.

(d) Application of the casing.

The tablets obtained as described were placed in a suitable container provided with regularly positioned circular cavities able to only partly contain a prepared tablet when positioned horizontally, to leave an exposed portion comprising a layer of active substance and the barrier.

Using a suitable spray system, the exposed surface of the tablets was sprayed with a solution consisting of:

| | |
|---|---|
| copolymer of acrylic and methacrylic acids (Eudragit S 110) | 5.0 g |
| castor oil | 0.5 g |
| acetone | 37.8 g |
| isopropanol | 56.7 g |

(e) "In vitro" evaluation of tablet characteristics.

(1) disintegration test.

The apparatus of U.S.P. XXI was used to evaluate the tablet disintegration rate. 6 tablets were placed in the baskets and the prescribed procedure was followed using gastric fluid (pH 1.2) at 37° C. as the disintegration fluid.

The first tablet layer containing the first medicament portion (35 mg) disintegrated in 5 minutes, after which time the second medicament portion contained in the third layer was completely unaltered, this portion being protected on its top by the gellable polymer barrier and on its sides and bottom by the impermeable and insoluble polymer membrane.

As the disintegration test proceeded a slow hydration of the barrier layer was noted, with an increase in volume of the barrier, gelling and weakening of the layer and slow erosion and/or solubilization.

During this stage the barrier layer became progressively permeable to the disintegration liquid, to enable water, after a time of about 0.5–1 hours, to come into contact with the second layer of the system containing the second portion of active principle.

When the water or aqueous fluid comes into contact with the third layer it swells to destroy the gelled barrier, with emergence of the indomethacin particles contained in the second layer. During the entire disintegration process the insoluble and impermeable polymer coating around the tablet preserves its characteristics and therefore at the end of the disintegration process it remains as a completely empty cylindrical container.

(2) Dissolution tests.

The "in vitro" tests to determine the release of active substance from the tablets were conducted using as the dissolution apparatus the six-position basket prescribed for the U.S.P. XXI disintegration test. 1000 ml of simulated intestinal fluid at pH 7.2 and at a temperature of 37° C. were used as the dissolution fluid. Using the tablets prepared as in Example 3, the following results were obtained:

| time (seconds) | percentage released (*) |
|---|---|
| 60 | 29.9% |
| 90 | 46.0% |
| 120 | 57.0% |
| 150 | 64.4% |
| 180 | 71.0% |
| 210 | 78.0% |
| (minutes) | |
| 35 | Membrane hydration |
| | percentage released (°) |
| 15 | 30.5% |
| 25 | 45.4% |
| 35 | 56.8% |
| 45 | 64.4% |
| 55 | 70.6% |
| 65 | 73.0% |
| 75 | 78.4% |

(*) Of the first portion of 35 mg of active substance contained in the first layer.
(°) Of the second portion of 35 mg of active substance contained in the third layer.

EXAMPLE 4

Preparation of tablets containing sodium naproxen as active substance (a) Preparation of sodium naproxen granulate.

To prepare 1000 tablets the following materials were used in the quantities stated:

| | |
|---|---|
| sodium naproxen | 275 g |
| corn starch | 40 g |
| methylcellulose | 1.5 g |
| sodium laurylsulphate | 1 g |

The sodium naproxen and corn starch sieved to 420μ were poured into a powder mixer and the mixture wetted with a 1.3% solution of methylcellulose in water containing the stated quantity of sodium laurylsulphate. The mixture when wetted homogeneously was forced through an 800μ screen to obtain a granulate which after partial drying was passed through a 420μ screen in accordance with the known art. The granulate was further dried in a tray drier until of constant weight, after which the following were added:

| | |
|---|---|
| sodium carboxymethylamide (Primojel) | 15 g |
| corn starch | 33 g |
| cross-linked polyvinylpyrrolidone (Polyplasdone) | 31 g |
| magnesium stearate | 4 g |

The component mixture was mixed until a homogeneous product was obtained.

(b) Preparation of barrier layer material.

The following were used to prepare barrier layers for tablet preparation:

| | |
|---|---|
| hydroxypropylmethylcellulose (low molecular weight-Methocel KM4) | 15.0 g |
| hydroxypropylmethylcellulose (medium molecular weight-Methocel K15M) | 5.0 g |
| mannitol | 40.0 g |
| talc | 28.0 g |
| polyvinylpyrrolidone | 12.0 g |
| yellow colouring | 2.0 g |
| Mg stearate | 1.0 g |

The hydroxypropylmethylcellulose, mannitol, talc and yellow colouring were mixed in a powder mixer; the mixture was wetted with a solution of polyvinylpyrrolidone in alcohol and the wet mass was forced through a 420μ screen. The granulate was dried in an oven and was then mixed with magnesium stearate.

(c) Preparation of sodium naproxen tablets.

The tablets were prepared without their casing using a multilayer tablet press with three loading stations; the first and third station were fed with the granulate containing sodium naproxen prepared as described under point (a), the second loading station being fed with the polymer granulate prepared for the barrier layer as indicated under point (b). The machine, fitted with circular flat punches of 13 mm diameter, was adjusted to feed a granulate quantity of 400 mg equivalent to 275 mg of active substance from stations 1 and 3 and a quantity of about 100 mg from station 2.

The machine pressure was adjusted to allow a pressure of about 3000 kg/cm² to be exerted in the final compression stage. Operating as described, at the end of the working cycle flat-based cylindrical tablets were obtained weighing about 900 mg and having two layers of active substance and a regular, homogeneous barrier separating the two layers of active substance.

(d) Application of the casing.

The tablets obtained as described were placed in a suitable container provided with regularly positioned circular cavities able to only partly contain a prepared tablet when positioned horizontally, to leave an exposed portion comprising a layer of active substance and the barrier.

Using a suitable spray system, the exposed surface of the tablets was sprayed with a solution consisting of:

| | |
|---|---|
| copolymer of acrylic and methacrylic acids (Eudragit S 100) | 5.0 g |
| castor oil | 0.5 g |
| acetone | 37.8 g |
| isopropanol | 56.7 g |

(e) "In vitro" evaluation of tablet characteristics.

(1) disintegration test.

The apparatus of U.S.P. XXI was used to evaluate the tablet disintegration rate. 6 tablets were placed in the baskets and the prescribed procedure was followed using gastric fluid (pH 1.2) at 37° C. as the disintegration fluid. The first tablet layer containing the first medicament portion (274 mg) disintegrated in 5 minutes, after which time the second medicament portion contained in the third layer was completely unaltered, this portion being protected on its top by the gellable polymer barrier and on its sides and bottom by the impermeable and insoluble polymer membrane.

As the disintegration test proceeded a slow hydration of the barrier layer was noted, with an increase in volume of the barrier, gelling and weakening of the layer and slow erosion and/or solubilization. During this stage the barrier layer became progressively permeable to the disintegration liquid, to enable water, after a time of about 0.5–1 hours, to come into contact with the second layer of the system containing the second portion of active principle.

When the water or aqueous fluid comes into contact with the third layer it swells to destroy the gelled barrier, with emergence of the sodium naproxen particles contained in the second layer. During the entire disintegration process the insoluble and impermeable polymer coating around the tablet preserves its characteristics and therefore at the end of the disintegration process it remains as a completely empty cylindrical container.

(2) Dissolution tests.

The "in vitro" test to determine the release of active substance from the tablets were conducted using as dissolution apparatus the six-position basket prescribed for the U.S.P. XXI disintegration test. 1000 ml of simulated intestinal fluid at pH 7.2 and at a temperature of 37° C. were used as the dissolution fluid. Using the tablets prepared as in Example 4, the following results were obtained:

| time (minutes) | Percentage released (*) |
|---|---|
| 2 | 23% |
| 4 | 41% |
| 6 | 53% |
| 8 | 68% |
| 10 | 78% |
| 35 | Membrane hydration |
| | Percentage released (°) |
| 5 | 49% |
| 10 | 70% |
| 15 | 88% |

(*) Of the first portion of 275 mg of active substance contained in the first layer.
(°) Of the second portion of 275 mg of active substance contained in the third layer.

EXAMPLE 5

Preparation of tablets containing ibuprofen as active substance (a) Preparation of ibuprofen granulate.

To prepare 4000 tablets the following materials were used in the quantities stated:

| | |
|---|---|
| ibuprofen | 600 g |
| corn starch | 80 g |
| methylcellulose | 3 g |
| sodium laurylsulphate | 2 g |

The ibuprofen and corn starch sieved to 420μ were poured into a powder mixer and the mixture wetted with a 1.3% solution of methylcellulose in water containing the stated quantity of sodium laurylsulphate. The mixture when wetted homogeneously was forced through an 800μ screen to obtain a granulate which after partial drying was passed through a 420μ screen in accordance with the known art. The granulate was further dried in a tray drier until of constant weight, after which the following were added:

| | |
|---|---|
| sodium carboxymethylamide (Primojel) | 30 g |
| corn starch | 66 g |
| cross-linked polyvinylpyrrolidone (Polyplasdone) | 12 g |
| magnesium stearate | 8 g |

The component mixture was mixed until a homogeneous product was obtained.

(b) Preparation of barrier layer material.

The following were used to prepare barrier layers for tablet preparation:

| | |
|---|---|
| hydroxypropylmethylcellulose (low molecular weight-Methocel KM4) | 60.0 g |
| hydroxypropylmethylcellulose (medium molecular weight-Methocel K15M) | 20.0 g |
| mannitol | 160.0 g |
| talc | 112.0 g |
| polyvinylpyrrolidone | 48.0 g |
| yellow colouring | 8.0 g |
| Mg stearate | 4.0 g |

The hydroxypropylmethylcellulose, mannitol, talc and yellow colouring were mixed in a powder mixer; the mixture was wetted with a solution of polyvinylpyrrolidone in alcohol and the wet mass was forced through a 420μ screen. The granulate was dried in an oven and was then mixed with magnesium stearate.

(c) Preparation of ibuprofen tablets.

The tablets were prepared without their casing using a multilayer tablet press with three loading stations; the first and third station were fed with the ibuprofen granulate prepared as described under point (a), the second loading station being fed with the polymer granulate prepared for the barrier layer as indicated under point (b). The machine, fitted with circular flat punches of 10 mm diameter, was adjusted to feed a granulate quantity of 200 mg equivalent to 150 mg of active substance from stations 1 and 3 and a quantity of about 65 mg from station 2.

The machine pressure was adjusted to allow a pressure of about 3000 kg/cm$^2$ to be exerted in the final compression stage. Operating as described, at the end of the working cycle flat-based cylindrical tablets were obtained weighing about 465 mg and having two layers of active substance and a regular, homogeneous barrier layer separating the two layers of active substance.

(d) Application of the casing.

The tablets obtained as described were placed in a suitable container provided with regularly positioned circular cavities able to only partly contain a prepared tablet when positioned horizontally, to leave an exposed portion comprising a layer of active substance and the barrier.

Using a suitable spray system, the exposed surface of the tablets was sprayed with a solution consisting of:

| | |
|---|---|
| copolymer of acrylic and methacrylic acid (Eudragit S 100) | 5.0 g |
| castor oil | 0.5 g |
| acetone | 37.8 g |
| isopropanol | 56.7 g |

(e) "In vitro" evaluation of tablet characteristics.

(1) disintegration test.

The apparatus of U.S.P. XXI was used to evaluate the tablet disintegration rate. 6 tablets were placed in the baskets and the prescribed procedure was followed using gastric fluid (pH 1.2) at 37° C. as the disintegration fluid. The first tablet layer containing the first medicament portion (175 mg) disintegrated in 5 minutes, after which time the second medicament portion contained in the third layer was completely unaltered, this portion being protected on its top by the gellable polymer barrier and on its sides and bottom by the impermeable and insoluble polymer membrane.

As the disintegration test proceeded a slow hydration of the barrier layer was noted, with an increase in volume of the barrier, gelling and weakening of the layer and slow erosion and/or solubilization. During this stage the barrier layer became progressively permeable to the disintegration liquid, to enable water, after a time of about 0.5–1 hours, to come into contact with the second layer of the system containing the second portion of active principle.

When the water or aqueous fluid comes into contact with the third layer it swells to destroy the gelled barrier, with emergence of the ibuprofen particles contained in the second layer. During the entire disintegration process the insoluble and impermeable polymer coating around the tablet preserves its characteristics and therefore at the end of the disintegration process it remains as a completely empty cylindrical container.

(2) Dissolution tests.

The "in vitro" test to determine the release of active substance from the tablets were conducted using as dissolution apparatus the six-position basket prescribed for the U.S.P. XXI disintegration test. 1000 ml of simulated intestinal fluid at pH 7.2 and at a temperature of 37° C. were used as the dissolution fluid. Using the tablets prepared as in Example 5, the following results were obtained:

| time (seconds) | Percentage released (*) |
|---|---|
| 15 | 1.5% |
| 45 | 5% |
| 75 | 13.3% |
| 105 | 28.6% |
| 135 | 45.3% |
| 165 | 60.5% |
| 195 | 69% |
| 225 | 75.6% |
| 255 | 80.6 |
| (minute) | |
| 35 | Membrane hydration |
| | Percentage raleased (°) |
| 8 | 7.3% |
| 18 | 9.0% |
| 28 | 10.3% |
| 38 | 23.0 |

| | -continued |
|---|---|
| 48 | 55.8 |
| 68 | 63.1% |
| 78 | 70.2% |
| 88 | 78.8% |

(*) Of the first portion of 150 mg of active substance contained in the first layer.
(°) Of the second portion of 150 mg of active substance contained in the third layer.

We claim:

1. A tablet for pharmaceutical use able to release an active substance at successive times, comprising:
   a first layer containing a first portion of an active substance, a disintegrant substance which on contact with water or aqueous liquids is able to develop a disintegrating force, and at least one excipient;
   a third layer containing a second portion of said active substance, a disintegrant substance, which on contact with water or aqueous liquid is able to develop a disintegrating force, and at least one excipient;
   a second layer comprising at least one polymeric material selected from the group consisting of cellulosic derivatives and polyvinyl alcohols, gellable or soluble on contact with water or an aqueous liquid, said second layer being interposed between the first and third layer;
   a casing comprising a film-forming polymeric material which is impermeable and insoluble in water having a pH of 7 or less which partially encapsulates the second layer and the third layer.

2. A tablet according to claim 1, wherein in the first layer the disintegrant substance is selected from the group consisting of carboxymethylamide, cross-linked sodium carboxymethylcellulose, cross-linked polyvinylpyrrolidone, cross-linked hydroxypropylmethyl cellulose, sodium bicarbonate, sodium carbonate and magnesium oxide.

3. A tablet according to claim 1, wherein the polymeric material of the second layer is selected from the group consisting of hydroxy propylcellulose methylcellulose and polyvinyl alcohols, and additionally contains at least one excipient selected from the group consisting of mannitol, talc, polyvinylpyrrolidone and magnesium stearate.

4. A tablet according to claim 1, wherein the casing comprises at least one polymeric substance selected from the group consisting of ethylcellulose, cellulose-acetatepropionate, methacrylate polymers, acrylic and methacrylic copolymers, and polyvinylalcohols.

5. A tablet according to claim 1, wherein said first and third layers each contain from 1% to 95% by weight of said disintegrant substance.

6. A tablet as claimed in claim 1, wherein at least one additional layer containing an active substance is present, and said additional layer is separated from said third layer by a barrier layer comprising at least one polymeric material selected from the group consisting of cellulosic derivatives and polyvinyl alcohols, said barrier layer being gellable or soluble on contact with water or an aqueous liquid.

7. A tablet as claimed in claim 1, wherein the active substance in the first layer is the same as the active substance in the third layer.

8. A tablet as claimed in claim 1, wherein the active substance in the first layer is different from the active substance in the third layers.

9. A tablet as claimed in claim 1, wherein said active substance is present in at least one of said first layer and said third layer in microencapsulated form.

10. A process for preparing the tablet of claim 1, comprising pressing said first, second, and third layer together to prepare a multilayer tablet, and applying said casing to said multilayer tablet.

11. A process as claimed in claim 10, wherein said casing is applied to said multilayer tablet by at least one method selected from the group consisting of spraying, compression, immersion, and inserting into a preformed casing.

* * * * *